(12) United States Patent
Yeh et al.

(10) Patent No.: US 8,784,820 B2
(45) Date of Patent: Jul. 22, 2014

(54) PLASMINOGEN-ACTIVATING ANTIBODY, USE AND PRODUCING METHOD THEREOF AND AGENT INCLUDING THE SAME

(71) Applicant: National Cheng Kung University, Tainan (TW)

(72) Inventors: Trai-Ming Yeh, Tainan (TW); Yung-Chun Chuang, Hsinchu (TW)

( * ) Notice: Subject to any disclaimer, the term of this patent is extended or adjusted under 35 U.S.C. 154(b) by 0 days.

(21) Appl. No.: 13/668,052

(22) Filed: Nov. 2, 2012

(65) Prior Publication Data
US 2013/0129744 A1 May 23, 2013

Related U.S. Application Data

(60) Provisional application No. 61/554,786, filed on Nov. 2, 2011.

(51) Int. Cl.
*A61K 39/42* (2006.01)
*A61K 39/00* (2006.01)
*A61K 39/12* (2006.01)
*A61K 39/193* (2006.01)

(52) U.S. Cl.
USPC .......... 424/147.1; 424/139.1; 424/159.1; 424/186.1; 424/218.1

(58) Field of Classification Search
None
See application file for complete search history.

(56) References Cited

PUBLICATIONS

Huang et al., "Antibodies against dengue virus E protein peptide bind to human plasminogen and inhibit plasmin activity," Clin Exp Immunol 110: pp. 35-40 (1997).*
Markoff et al., "Development of Cross-Reactive Antibodies to Plasminogen during the Immune Response to Dengue Virus Infection," Journal of Infectious Diseases, 164: pp. 294-301 (1991).*
Yng-Huey Huang et al., "Activation of coagulation and fibrinolysis during dengue virus infection", J Med Virol., 2001, vol. 63, p. 247-251.
Byron E. E. Martina et al., "Dengue virus pathogenesis: an integrated view", Clinical Microbiology Reviews, 2009, vol. 22, p. 564-581.

* cited by examiner

*Primary Examiner* — Michelle S. Horning
*Assistant Examiner* — M. Franco Salvoza

(57) ABSTRACT

An antibody for activating plasminogen is provided. The antibody is produced from a hybridoma cell line deposited on Nov. 24, 2011 under accession number BCRC 960433 at Food Industry Research and Development Institute, 331 Shih-Pin Road, Hsinchu 300, Taiwan. The uses and producing method of the antibody, and an agent including the antibody used for treating stroke, myocardial infarction or syndromes cause by thrombus are also disclosed.

7 Claims, 6 Drawing Sheets

PLASMINOGEN-ACTIVATING ANTIBODY, USE AND PRODUCING METHOD THEREOF AND AGENT INCLUDING THE SAME

CROSS REFERENCE TO RELATED APPLICATIONS

This Non-provisional application claims priority to U.S. provisional patent application Ser. No. 61/554,786 filed on Nov. 2, 2011. This and all other extrinsic materials discussed herein are incorporated by reference in their entirety.

BACKGROUND OF THE INVENTION

1. Field of Invention

The present invention relates to an antibody, use and producing method thereof and agent including the same, and more particularly, to a plasminogen-activating antibody, use and producing method thereof and agent including the same.

2. Related Art

Acute disorder, like stroke and cardiac disease, caused by arterial embolization may cause permanent nerve damage and coma. Moreover, without instant diagnosis and treatment, it may cause other complications and death. In United States of America, stroke has become the third leading cause of adults, and the same as Europe, stroke is also the first leading cause causing disabilities of adults. And the cardiac disease has become the first cause of death in the world. It has great influence around the world.

The main cause of stroke and cardiac disease is the formation of thrombus. Roughly speaking, thrombus is generated after injury and fracturing of artery, and its major component are mostly fibrin. Hence, as mentioning how to prevent and treat stroke and cardiovascular disorder, many kinds of techniques have been focused on promoting the fibrinolysis of plasmin. Plasmin is converted after the activation of plasminogen by tissue plasminogen activator (tPA) and urokinase plasminogen activator (uPA); otherwise, the plasmin is able to promote the fibrolysis of fibrin. With respect to the mechanism, the prior technique is focused on promoting the activation of plasminogen by intravenously injecting tPa or additionally providing hiruding to break down the fibrin and to clean the thrombus. Although the method mentioned above is able to give first-aid treatment, it most likely to induce severe side effects of bleeding.

Therefore, it is an important subject in the medical field to provide a treatment mean in contrast to the above-mentioned pathogenic mechanism, and cleaning the thrombus by plasminogen to achieve the efficacies of treating or preventing relevant disease.

SUMMARY OF THE INVENTION

In view of the foregoing, it is an object of the present invention to provide a plasminogen-activating antibody able to promote the fibrolysis of the fibrin to treat or prevent relevant disease, its use and manufacturing method, and the agent having the same.

To achieve the above, the present invention discloses a plasminogen-activating antibody formed by hybridoma cell line deposited on Nov. 24, 2011 under accession number BCRC 960433 at the Food Industry Research and Development Institute, 331 Shih-Pin Road, Hsinchu 300, Taiwan and also on Nov. 14, 2013 under accession number DSM ACC3219 at Leibniz-Institut Dsmz-Deutsche Sammlung von Mikroorganismen and Zellkulturen GmbH, Inhoffenstr. 7B, D-38124 Braunschweig, Germany.

The term "hybridoma cell line" used here is collectively referred to the fusion of two cells and the continuous proliferation after fusion. One of them is able to generate specific antibody and collected from animal, like lymphocytes. The term "animal" used above is collectively referred to an animal host able to be affected by any seratypes of dengue virus, and it is preferably to be mammals like human, monkey, mouse, cow, sheep, dog, cat or pig.

In one embodiment of the present invention, the hybridoma cell line is fused by myeloma cells and Dengue virus immunolized splenocyte.

In one embodiment of the present invention, the antibody having specificity for an amino acid sequence, the amino acid comprises at least Leu-Pro-X-Pro, and X is any one of amino acid residues.

In one embodiment of the present invention, the antibody also comprises the binding ability with dengue virus E protein and the plasminogen.

In one embodiment of the present invention, the antibody activates the plasminogen by activity of the serine protease to form plasmin.

In one embodiment of the present invention, the antibody coacts with the activator of the plasminogen.

The present invention further provides a use of an antibody for treatment or prevention of stroke, myocardial infarction or syndromes cause by thrombus. The term "treatment" used here is collectively referred to the offering of a specific substance to one organism diagnosed with syndromes like stroke or myocardial infarction caused by clotting of blood or fibrin or the inclination of the above-mentioned syndromes, and after providing the specific substance, the syndromes are removed, mitigated, cured, improved, relieved or alleviated, or even prevented from the deterioration of the syndromes. Otherwise, the present invention further provides a use of the antibody mentioned above used for fusing the fibrin.

The present invention further provides an agent for treating stroke, myocardial infarction or syndromes caused by thrombus. It comprises at least the antibody mentioned above.

The present invention further provides a manufacturing method of antibody of plasminogen comprising the steps of: immunolizing an animal by dengue virus; fusing an antibody of the animal to generate cells and myeloma cells; and selecting a hybridoma of an antibody having the specificity for an E protein of a dengue virus or plasminogen, so as to collect the antibody.

In one embodiment of the present invention, the E protein of the dengue virus or plasminogen comprises an amino acid sequence, and the amino acid sequence comprises at least Leu-Pro-X-Pro, and the X is any one of amino acid residues.

In one embodiment of the present invention, the antibody activates the plasminogen by activity of a serine protease to form plasmin.

In one embodiment of the present invention, the manufacturing method coacts with the activator of the plasminogen.

As mentioned above, the antibody provided by the present invention is able to bind plasminogen and to transfer into plasmin by activating plasminogen, and then, degrading the plasmin and/or fibrin with the enzyme activity of plasmin. Hence, the thrombus and other fibrin coagulum can be broken down and prevent from accumulation and blood flow blocking. That is, the antibody provided by the present invention can be applied to treat or prevent stroke, myocardial infarction or other diseases caused by thrombus, and further replacing the conventional treatment means with high risk and side effects to raise life quality.

BRIEF DESCRIPTION OF THE DRAWINGS

The present invention will become more fully understood from the subsequent detailed description and accompanying drawings, which are given by way of illustration only, and thus are not limitative of the present invention and wherein.

DETAILED DESCRIPTION OF THE INVENTION

Figure 1:
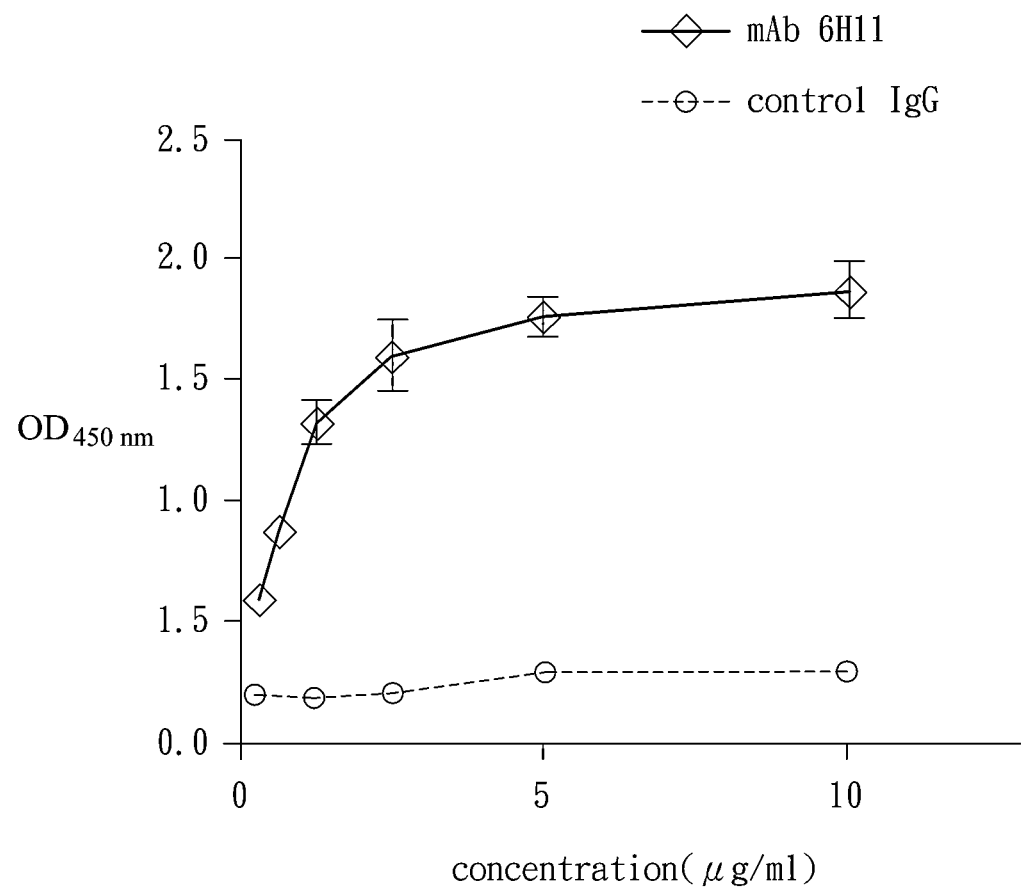
FIG. 1 is a testing chart of the result of the specificity to dengue virus and plasminogen of 6H11 mAb of the present invention.

The present invention will be apparent from the following detailed description, which proceeds with reference to the accompanying drawings, wherein the same references relate to the same elements.

One of the experiments of the present invention verifies that animal body infected by Dengue virus is able to generate specific antibody to Dengue virus (DENY). The epitope recognized by an antibody specific to the E protein of Dengue virus is the same as one amino acid sequence of the plasminogen (plg) in the animal body. The antibody is able to combine with plasminogen simultaneously, and the animal is mouse.

The amino acid sequence mentioned above includes Leu-Pro-X-Pro, and the X can be any one of amino acid residues, preferably leucine or serine.

Due to the catalytic capability of the antibody, the antibody is able to make one fragment of the plasminogen splitted out after its combination with plasminogen, and transferring to a plasmin with fusing ability of fibrin. In one embodiment of the present invention, the antibody comprises the activity of serine protease or serine proteinase. The antibody makes the plasminogen form plasmin through the activated serine in the amino acid sequence.

Acute syndromes caused by stroke, coronary artery heart disease and myocardial infarction are triggered by the blocking of arteries with fibrin and thrombus. Thus, the present invention provides an antibody having the above-mentioned features. With the function of activating plasminogen, the antibody is able to transfer into plasmin and promote or strengthen the generation of the fibrolysis of fibrinogen and fibrin in order to treat or prevent the above-mentioned disease or syndromes.

According to one embodiment of the present invention, the splenocyte immunolized by dengue virus and possessing the ability of making antibody are isolated from mouse, and further fusing with myeloma cell line, and then collecting the hybridoma cells. With immunological method like ELISA and selection of the antibody specific to both of the E protein and plasminogen of dengue virus simultaneously, corresponding hybridoma cells are selected. The method of manufacturing hybridoma and subsequent selection of antibody are well-understood by the person having ordinary skill in the art, and are not repeated here. The monoclonal antibody(mAb) capable of recognizing both of the E protein and plasminogen of dengue virus simultaneously is named 6H11. The sequences of mAb is listed as the sequence table SEQ ID NO: 1, and the hybridoma cells manufacturing the monoclonal antibody 6H11 were deposited on Nov. 24, 2011 under accession number BCRC 960433 at the Food Industry Research and Development Institute, 331 Shih-Pin Road, Hsinchu 300, Taiwan and also on Nov. 14, 2013 under accession number DSM ACC3219 at Leibniz-Institut Dsmz-Deutsche Sammlung von Mikroorganismen and Zellkulturen GmbH, Inhoffenstr. 7B, D-38124 Braunschweig, Germany. The antibody and the hybridoma cells are examples for illustrating the content of the present invention, but not for the limitation.

In the experiment of the present invention, the amount of plasmin in the mouse body increases after the monoclonal antibody is provided to the mouse. Otherwise, the concentration of the product of the fibrolysis (like D-dimer) of the fibrin also increases. Accordingly, the monoclonal antibody generated by the hybridoma cell lines deposited on Nov. 24, 2011 under accession number BCRC 960433 at the Food Industry Research and Development Institute, 331 Shih-Pin Road, Hsinchu 300, Taiwan and also on Nov. 14, 2013 under accession number DSM ACC3219 at Leibniz-Institut Dsmz-Deutsche Sammlung von Mikroorganismen and Zellkulturen GmbH, Inhoffenstr. 7B, D-38124 Braunschweig, Germany, has the effect for treating or preventing stroke, myocardial infarction or syndromes cause by thrombus. In addition, the monoclonal antibody of the present invention also comprises the use of fusing fibrin.

The Antibody of the present invention can be provided for the patient by intravenous injection, intraperitoneal injection, or even injecting in the affected area. The term "patient" used here is collectively referred to the person with the syndromes of blood clotting or the acute syndromes caused by thrombus like stroke or myocardial infarction; or even referred to those with blood clotting symptoms but without the induction of other complications like stroke or myocardial infarction. Specifically speaking, the term "patient" use is here is referred to mammals, preferably human. Otherwise, in the treatment or prevention of stroke, myocardial infarction, or other syndromes cause by thrombus, the usage dose may be different with the severity of syndromes, the clotting level of fibrin, the level of blot clotting, the clotting level of artery and animals. For example, the usage dose for mouse will increase 1~5 μg antibody per gram according to the body weight.

In one embodiment of the present invention, the antibody is able to coact with cofactors for promoting fibrolysis. Those cofactors not only posses the activity for activating the plasminogen to form plasmin used for promoting fibrolysis, but speed up the formation of plasmin generated by plasminogen. The plasminogen activator comprises tissue plasminogen activator (tPA) and urokinase plasminogen activator (uPA). Preferably, plasminogen activator is uPA.

As TABLE 1 illustrating, the previous experiment obtain 6 mAbs specific to plasminogen and the mAb combined to E protein of dengue virus simultaneously, especially the 6H11 mAb. The hybridoma cell forming the 6H11 mAb has been deposited on Nov. 24, 2011 under accession number BCRC 960433 at the Food Industry Research and Development Institute, 331 Shih-Pin Road, Hsinchu 300, Taiwan and also on Nov. 14, 2013 under accession number DSM ACC3219 at Leibniz-Institut Dsmz-Deutsche Sammlung von Mikroorganismen and Zellkulturen GmbH, Inhoffenstr. 7B, D-38124 Braunschweig, Germany. With reference to the data in FIG. 1, the 6H11 mAb was able to combine with the plasminogen with specificity and the combination was dose-dependent.

Hence, the following experiment takes the 6H11 mAb for example to specify more contents.

In one embodiment of the present invention, the agent further includes an activator, a stabilizer, a surfactant, an antioxidant and/or a preservative or an activator of plasminogen. The stabilizer may be composed of glycine, methionine, cysteine hydrochloride monohydrate, leucine, HCl-lysine, HCl-arginine, asparatic acid or its sodium chloride to prolong the preservation of the agent. Isotonic substance like polyhydric alcohol or buffer like glutamate, succinate, citric acid and other organic buffer salt are used to adjust the pH value in the physiological environment of the animal. Otherwise, the plasminogen activator may coact with the antibody of the present invention to assist the formation of plasmin from plasminogen inside the animal body, thus raising the speed of cleaning thrombus. The plasminogen activator may be one of the tPA or uPA, or even both of the two. In addition, the content of the antibody of the agent may be different with severity of symptoms, clotting level of fibrin, severity of blood clotting, blocking level of artery, condition of different patient and approaches of injection. Of course, other component can be adjusted with the ratio of antibody.

The injection pathway of agent may be vein, artery, muscle, bursa, peritoneal cavity, brain, or even mouth according to the condition of patients, the affected area, the carrying and delivering method of the carrier and the effective time. In one embodiment of the present invention, the intravenous injection method is applied to the subject.

The present invention further provides a manufacturing method of antibody of plasminogen. The method includes the following steps: immunolizing an animal by dengue virus; fusing an antibody of the animal to generate cells and myeloma cells; and selecting a hybridoma of an antibody having the specificity for an E protein of a dengue virus or plasminogen, and collecting the antibody. The detail description of the first two steps has been explicated above. And the third step of the method is well-understood by the person having ordinary skill in the art, and is not repeated here. The only thing needed to specify is the antibody mentioned-above is preferably specific to the E protein of the dengue virus and plasminogen simultaneously.

The antibody formed by the manufacturing method of the present invention has the same feature with the above-mentioned one, and is not repeated here.

The following and accompanying figures take a number of experiments for examples to describe the main details of a plasminogen-activating antibody, the use and the manufacturing method applying the same, and the agent having the same, and to verify the effect of the antibody for treating stroke, myocardial infarction and syndromes caused by thrombus.

Experiment 1

Manufacturing the mAbs Specific to the E Protein of Dengue Virus and Plasminogen Patients' Sera Sera were obtained from 32 dengue patients of DENV type 2 infections and 48 DENV-3-infected patients. Otherwise, Hepatitis C (HCV) sera were obtained from 20 patients, and normal human sera were obtained from 14 healthy donors as controls. The detailed description of the virus purification are well-understood by the person having ordinary skill in the art, and is not repeated here.

Immunolizing the Mouse by Dengue Virus, and Manufacturing the Hybridoma Cells to Form Specific mAbs 5 6-week-old female BALB/c mice were immunized with 50 μg DENV in Complete Freund's Adjuvant intraperitoneally and boosted in PBS 3 times every 2 weeks. 3 days before fusion, the mice were injected intravenously with 50 μg antigen in PBS. The hybridomas were generated by ClonaCell-HY kit (Stemcell Technologies Inc., Vancouver, BC, Canada) according to the manufacture's procedure. Briefly, the splenocytes were fused with FO cells and selected by HAT-based selection medium.

Limiting dilution was performed to obtain single colonies. Supernatants from single colonies were collected and screened for antibodies against DENV by enzyme-linked immunosorbent assay (ELISA). The isotype of these mAbs were determined by Monoclonal Antibody Isotyping Kit (Santa Cruz Biotechnology, Santa Cruz, Calif.). To isolate mAbs, hybridomas were injected to pristine-primed BALB/c mice for 7 to 10 days. IgG and IgM mAbs were purified from ascites by protein G sepharose beads (GE Healthcare, Sweden) or protein L resin (GenScript Corp., Piscataway, N.J.), respectively. MAbs were dialyzed against PBS (pH 7.4) and stored at −20° C.

Using ELISA to Test the Specificity of mAbs to Dengue Virus

For ELISA, 50 μl of Plg (5 μg/ml) or DENV (5 μg/ml) in 0.5 M carbonate/bicarbonate coating buffer (pH 9.6) were coated onto 96-well ELISA plate (GeneDireX, Las Vegas, Nev.) at 4° C. overnight. The wells were blocking by 1% BSA in PBS. mAbs were incubated on wells at 37° C. for 1 h. Horseradish peroxidase (HRP)-conjugated goat secondary antibodies against mouse (Zymed, San Francisco, Calif.) was diluted in 5,000× fold and incubated. The color was developed using tetramethylbenzidine (TMB) as the substrate for 10 mins, and sulfuric acid (2N) was used to terminate the reaction. The absorbance was read at optical density (OD) 450 nm.

The present invention further provides an agent used for treating stroke, myocardial infarction or syndromes cause by thrombus. The agent includes the plasminogen-activating antibody formed by a hybridoma cell line deposited on Nov. 24, 2011 under accession number BCRC 960433 at the Food Industry Research and Development Institute, 331 Shih-Pin Road, Hsinchu 300, Taiwan and also on Nov. 14, 2013 under accession number DSM ACC3219 at Leibniz-Institut Dsmz-Deutsche Sammlung von Mikroorganismen und Zellkulturen GmbH, Inhoffenstr. 7B, D-38124 Braunschweig, Germany. The antibody is preferably the 6H11 antibody. More preferably the amino sequence of the antibody is at lease 85% the same as the sequence table SEQ ID NO: 1, still more preferably is at least 90%, or yet still more preferably is at least 95%. The other property of the antibody is the same as the above-mentioned one, and is not repeated here.

TABLE 1

| | 2A12 | DD1 | 8E5 | 6H11 | 6E11 | 7D2 |
|---|---|---|---|---|---|---|
| DENV | ● | ● | ● | ● | ● | ● |
| Epitope | E | E | E | E | E | E |
| Isotype | IgG2b-k | IgG1-k | IgM-k | IgG3-k | IgG1-k | IgM-k |

Experiment 2

Amino Acid Sequence L-P-X-P Recognition by 6H11 mAb

The amino sequence of the epitope of mAb was mapped by phage-displayed random peptide library kit, PhD 12-mer, New England Biolabs, Ipswich, Mass. The method of phage-displayed random peptide library kit and the phage library are well-understood by the person having ordinary skill in the art, and are not repeated here. And then, DNA sequence of a positive phage able to specifically combining with mAb was analyzed.

The result is showed in TABLE 2 and TABLE 3. There were 10 phages exhibiting the epitopes recognizable of the 6H11 mAb. 9 of the above phages comprised the same sequence, and only the sequence of phage No. 2 had a minor difference with others. These epitopes shared a same motif, L-P-X-P. Likewise, the motif appeared in the amino acid 216 to 219 in the DENV-1, DENV-2 and DENV-4, amino acid 214 to 217 in the DENV-3, and amino acid 686 to 689 in the plasminogen. Apparently, the amino acid sequence specifically recognized by mAb is L-P-X-P, and the sequence is simultaneously exists in the E protein of dengue virus and plasminogen.

TABLE 2

| Item | Amino Acid sequence |
|---|---|
| Phage 1,3-10 | I P M P W G P A W T A H |
| DENV-NS1(264-275) | I T G P W H L G K L E M |
| DENV-1 E(213-227) | F L D L P L P W T S G A S T S |
| DENV-2 E(213-227) | F L D L P L P W L P G A D/T T Q |
| DENV-3 E(211-225) | F F D L P L P W R S G A T T E |
| DENV-4 E(213-227) | F L D L P L P W T A D G A D T |
| Plg(683-697) | P A C L P S P N Y V V A D R T |

TABLE 3

| Item | Amino Acid sequence |
|---|---|
| Phage 2 | L P Q P W G P A W S A H |
| DENV-NS1(264-275) | I T G P W H L G K L E M |
| DENV-1 E(213-227) | F L D L P L P W T S G A S T S |
| DENV-2 E(213-227) | F L D L P L P W L P G AD/TT Q |
| DENV-3 E(211-225) | F F D L P L P W R S G A T T E |
| DENV-4 E(213-227) | F L D L P L P W T A D G A D T |
| Plg(683-697) | P A C L P S P N Y V V A D R T |

With reference to experiment 1 and 2, because the 6H11 mAb is able to specifically recognize the amino acid L-P-X-P, it comprises the combination ability to E protein of dengue virus and plasminogen.

Experiment 3

6H11 mAb Activity Determination

1 μM of plasminigen were incubated with mAbs (30 μg/ml or 150 μg/ml) from 1 to 24 h. The mixtures were then incubated with 1 mM S-2251 (551.6 μg/ml). The kinetic change of optical density (OD) at 405 nm was measured.

Figure 2A:
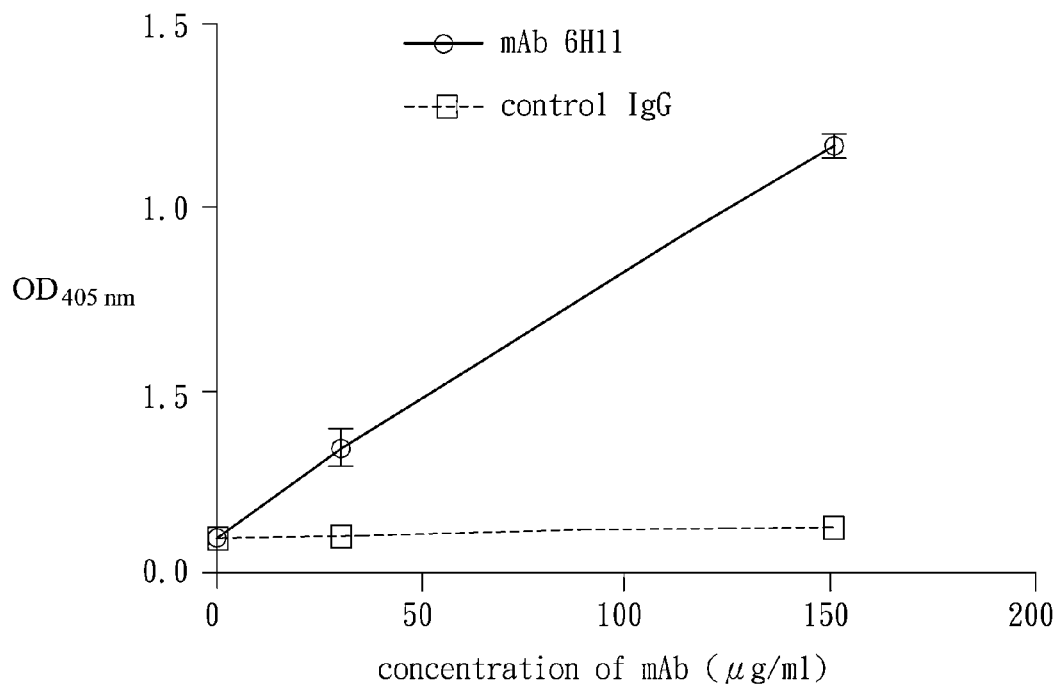
FIG. 2A is the chart of the dose-dependent analysis of the 6H11 mAb for activating the plasminogen of the present invention.
Figure 2B:
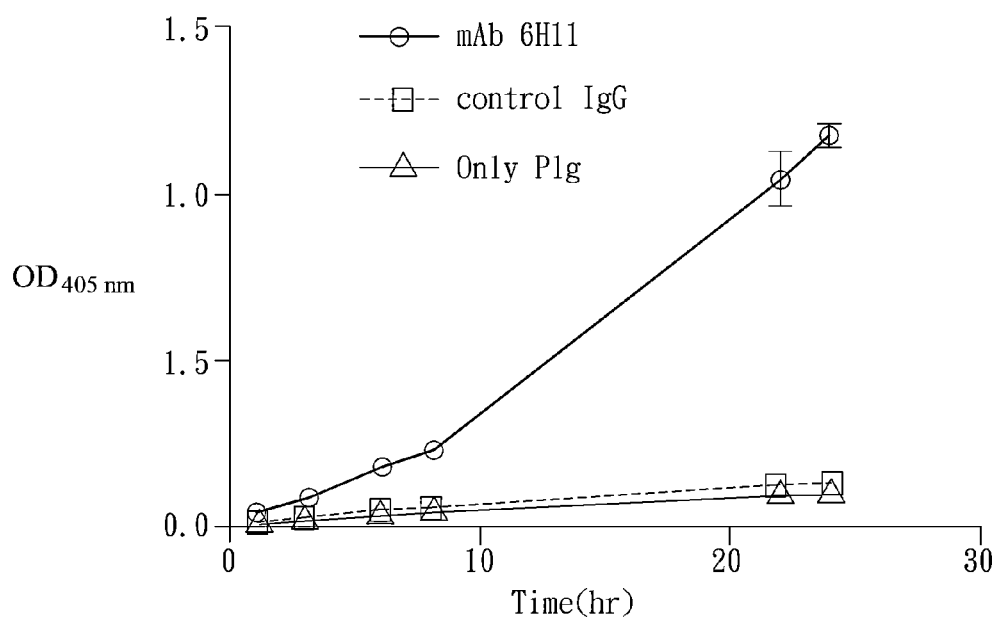
FIG. 2B is the chart of the time-dependent analysis of the 6H11 mAb for activating the plasminogen of the present invention.

FIG. 2A and FIG. 2B shows the result of the conversion of plasminogen to plasmin by the cross-reaction of plasminogen and 6H11 mAb in a dose-dependent manner and time-dependent manner. Obviously, compared to the IgG group or the control group, the optical density (OD) at 405 nm of 6H11 mAb increased continuously. That is, with the increase of the dose and time of the 6H11 mAb, the reaction of plasmin converted by plasminogen activated by 6H11 mAb and the substrate S-2251 brings the result.

Serine Protease Activity of 6H11 mAb Determination

Otherwise, the serine protease activity of mAbs was measured using serine protease chromogenic substrate S-2288. The antibodies (30 μg/ml, 150 μg/ml, or 300 μg/ml) were incubated with S-2288 (1 mM, 577.6 μg/ml) with or without the presence of different concentrations of Roche Complete protease inhibitor cocktail (Roche Diagnostics Ltd, Mannheim, Germany) for 2 to 24 h. The OD value was detected as described above.

Figure 2C:
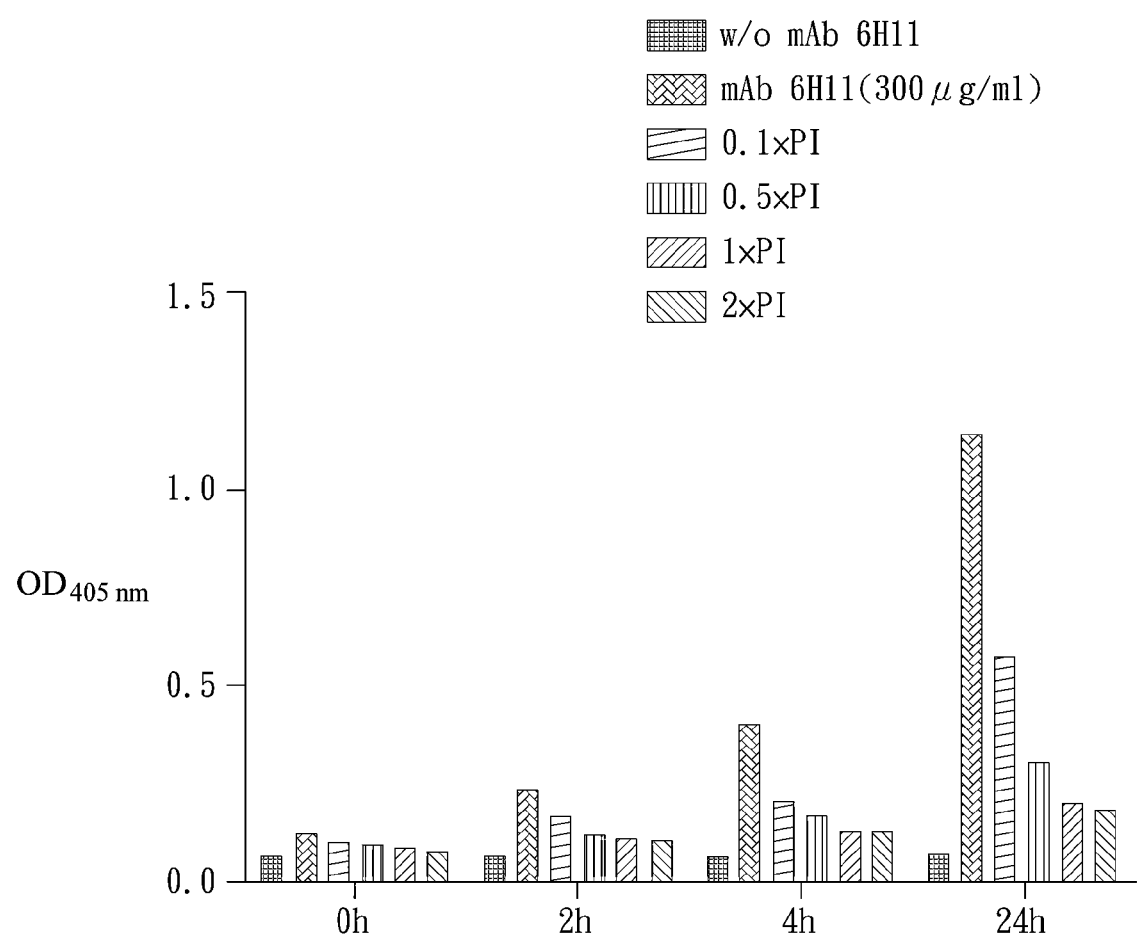
FIG. 2C is the chart of the analysis of the serine protease activity of 6H11 mAb of the present invention.

The result is referred to FIG. 2C. With the addition of protease inhibitor, the OD value would not increase with time. That means, protease inhibitor could inhibit 6H11 mAb to hydrolyze S-2288 in a dose-dependent manner, and thus verifying that the 6H11 mAb has the serine protease activity.

The Enhancement of 6H11 mAb by the Activator of Plasminogen Determination

1 μM of Plasminogen and urokinase (3 U/ml final concentration; Sigma-Aldrich) were co-incubated with mAbs (30 μg/ml) from 1 to 120 mins. The mixtures were then incubated with 1 mM chromogenic substrate S-2251 (551.6 μg/ml). The kinetic change of optical density (OD) at 405 nm was measured.

Figure 2D:
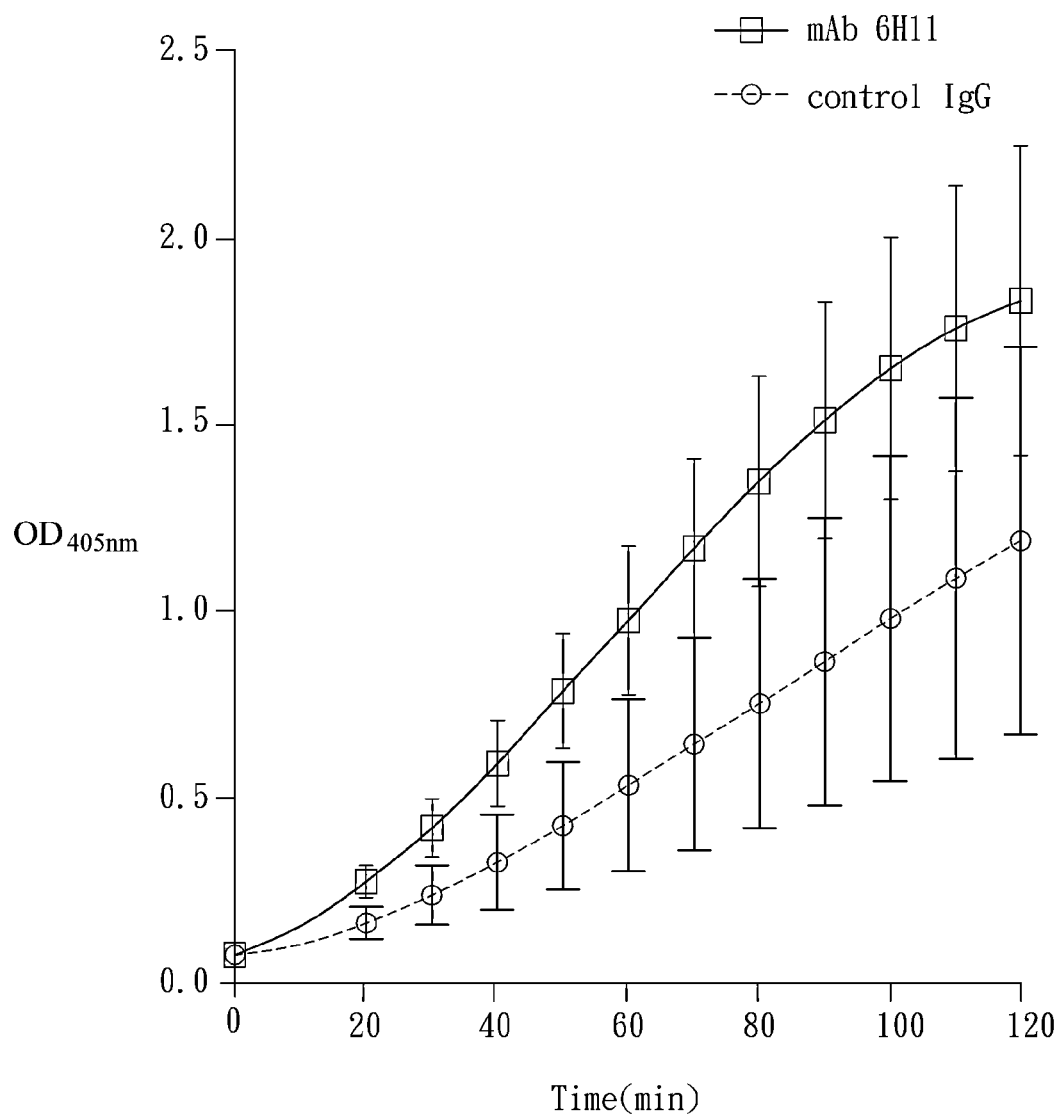
FIG. 2D is the chart of the activation speed of plasminogen promoted by the coactions of 6H11 mAb and urokinase of the present invention.

Compared to FIG. 2B showing the result of 2 hours reacting, the OD value shown in FIG. 2D showed significant enhancement when the mAbs 6H11 reacted with urokinase for 120 mins. Apparently, the addition of urokinase is able to improve the hydrolysis of chromogenic substrate S-2251, which indicated the existence of urokinase may accelerate the conversion of plasmin from plasminogen.

Fibrinogen (Fbg) Cleavage Analysis

MAb (100 ug/ml) were pre-incubated with 1 μM plasminogen (plg) for 36 h at 37° C. The other two groups use urokinase (3 U/ml final concentration; Sigma-Aldrich) or non-specific IgG as substitution for mAbs 6H11 to react with plasminogen.

The groups mentioned above were also incubated with Fbg (100 μg/ml) for additional 12 h, respectively. The mixtures were analyzed by 10% SDS-PAGE followed by western blotting. For western blotting, Fbg fragment was detected using 1:3000 diluted rabbit anti-Fbg beta and gamma chain polyclonal antibody (GeneTex, San Antonio, Tex.) followed by a 1:10,000 diluted HRP-conjugated goat anti-rabbit immunoglobulin antibody (Sigma-Aldrich). And then, the result of chromogenic reaction was observed.

Figure 2E:
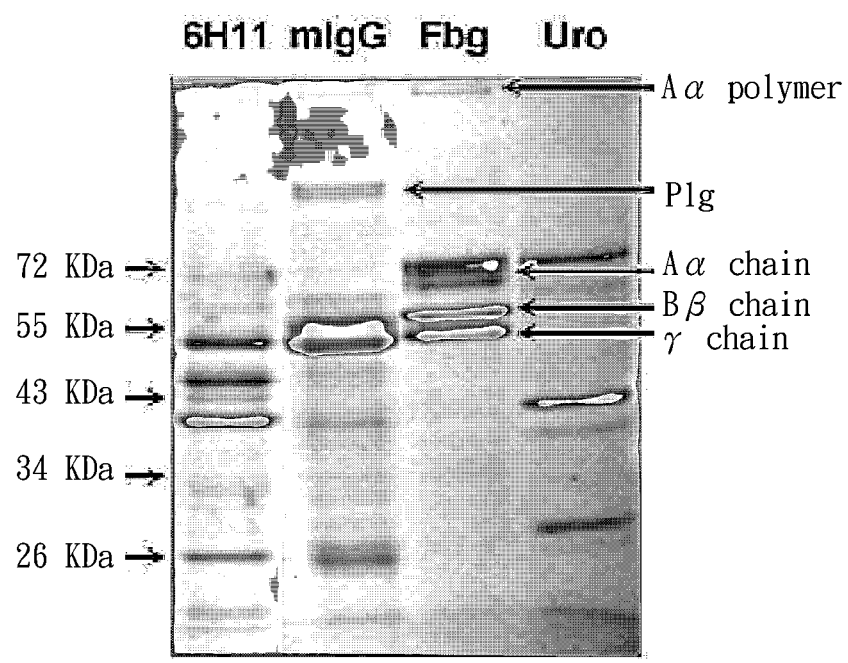
FIG. 2E is an experimental result of the fibrinogen fibrolysis by the 6H11 mAb of the present invention.

The result was shown in FIG. 2E, After the plasminogen and the fibrinogen coculture with 6H11 mAb, the four main bands in fibrinogen including Aα-polymer, Aα chain, Bβ chain, and γ chain were decomposed into small fragments. In urokinase-treated group, these bands were decomposed significantly.

Experiment 3

Measurement of mAbs-Induced Plasminogen Activity and D-Dimer Formation in Mice

Eight six-week-old BALC/c female mice (purchased and maintained at the Laboratory Animal Center of National Cheng Kung University) were used.

Five BALC/c mice and three BALB/c mice were intravenously injected with 50 μl 6H11 mAb(2.5 μg/g body weight) and control IgG, respectively. Blood (400 μl) of mice was collected into tubes which contained 100 μl 3.2% sodium citrate. PPP in blood was harvest by centrifugation at 2,500×g for 15 mins. For Plm activity assay, 10 μl PPP was incubated with S-2238 (1 mM) for 2 hours. The OD value at 405 nm was recorded by VersaMax microplate reader. To determine D-dimer level, competition-based mice D-dimer ELISA kits were used (BlueGene; Shanghai, China).

Figure 3A:
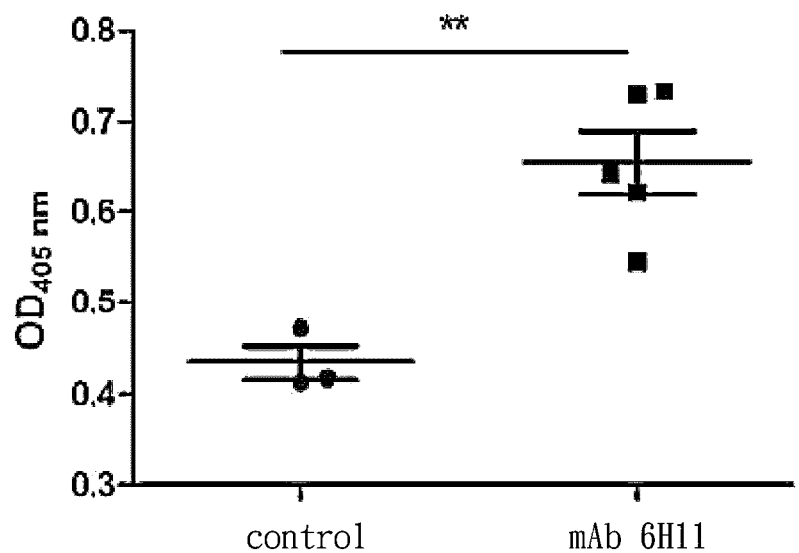
FIG. 3A is the chart of the plasminogen variation after the 6H11 mAb injected into the mice of the present invention.

As shown in FIG. 3A, the OD405 value measured in mAbs group were 1.5-fold higher than those treated with control IgG. The plasminogen activity of mice treated with mAb 6H11 were also significantly higher than those treated with control IgG.

Figure 3B:
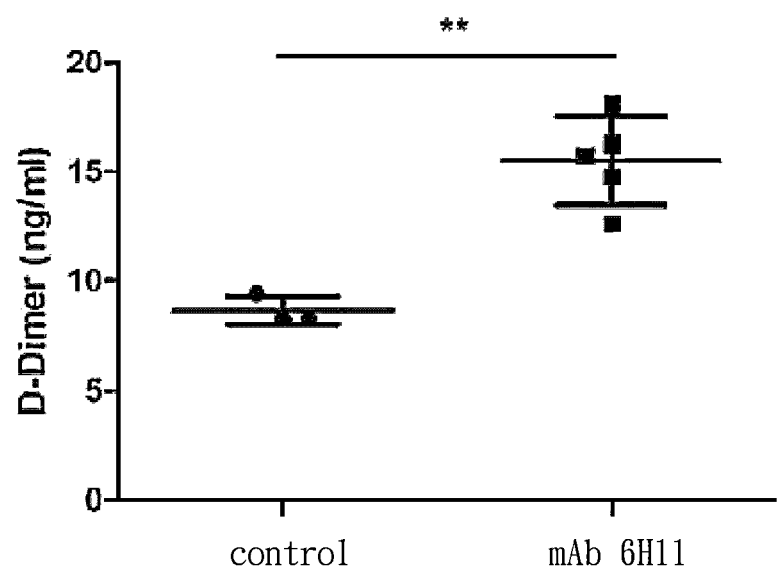
FIG. 3B is the chart of the D-dimer variation after the 6H11 mAb injected into the mice of the present invention.

The condition of D-dimer formation of mice injected with mAbs was shown in FIG. 3B, The D-dimer of the control group was approximately 8.668±0.3679 ng/ml, and the D-dimer of the mAb group was approximately 15.52±0.9072 ng/ml (p=0.0015). Apparently, 6H11 mAb injection increase the D-dimer in the mice.

D-dimer is the by-product of fibrin degradation. Hence, referring to the result of experiment 3, 6H11 mAb is able to promote the activation of plasminogen to form fibrinogen, and degrading the fibrinogen and fibrin.

All statistical data provided by the present invention were collected from three times repeated trials, the numerical value were taken an average±SD (standard deviation). Student's t test is used to determine the significant differences between the experiment group and control group. P<0.005 means the two groups exist significant differences.

As mentioned above, the antibody provided by the present invention is able to bind plasminogen and to transfer into plasmin by activating plasminogen, and then, degrading the plasmin and/or fibrin with the enzyme activity of plasmin. Hence, the thrombus and other fibrin coagulum can be broken down and prevent from accumulation and blood flow blocking. That is, the antibody provided by the present invention can be applied to treat or prevent stroke, myocardial infarction or other diseases caused by thrombus, and further replacing the conventional treatment means with high risk and side effects to raise life quality.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A plasminogen-activating antibody formed by hybridoma cell line, wherein the hybridoma cell line is deposited on Nov. 24, 2011 under accession number BCRC 960433 at the Food Industry Research and Development Institute, 331 Shih-Pin Road, Hsinchu 300, Taiwan and also on Nov. 14, 2013 under accession number DSM ACC3219 at Leibniz-Institut Dsmz-Deutsche Sammlung von Mikroorganismen and Zellkulturen GmbH, Inhoffenstr. 7B, D-38124 Braunschweig, Germany.

2. The antibody according to claim 1, wherein the hybridoma cell line is fused by myeloma cells and Dengue virus immunolized splenocyte.

3. The antibody according to claim 1, wherein the antibody has specificity for an amino acid sequence comprising at least Leu-Pro-X-Pro, and X is any amino acid residue.

4. The antibody according to claim 1, wherein the antibody also comprises binding ability with dengue virus E protein and the plasminogen.

5. The antibody according to claim 1, wherein the antibody activates the plasminogen by activity of the serine protease to form plasmin.

6. The antibody according to claim 1, wherein the antibody acts with the activator of the plasminogen.

7. An agent for treating stroke, myocardial infarction or syndromes caused by thrombus comprising the antibody according to claim 1.

* * * * *

SEQUENCE LISTING

```
<160> NUMBER OF SEQ ID NOS: 1

<210> SEQ ID NO 1
<211> LENGTH: 250
<212> TYPE: PRT
<213> ORGANISM: Mouse sp.
<220> FEATURE:
<221> NAME/KEY: misc_feature
<223> OTHER INFORMATION: Mouse hybridoma cell line
<220> FEATURE:
<221> NAME/KEY: Peptide
<222> LOCATION: (1)..(250)

<400> SEQUENCE: 1

Asp Ile Val Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Leu Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln His Tyr Asp Ser Tyr Pro Leu
                85                  90                  95

Thr Phe Gly Ala Gly Thr Lys Leu Glu Ile Lys Ser Ser Gly Gly Gly
            100                 105                 110

Gly Ser Gly Gly Gly Gly Gly Ser Ser Arg Ser Ser Leu Glu Val
        115                 120                 125

Gln Leu Gln Gln Ser Gly Gly Leu Val Gln Pro Gly Gly Ser Arg
    130                 135                 140

Lys Leu Ser Cys Ala Ala Ser Gly Phe Thr Phe Ser Ser Phe Gly Met
145                 150                 155                 160

His Trp Val Arg Gln Ala Pro Glu Lys Gly Leu Glu Trp Val Ala Tyr
                165                 170                 175

Ile Ser Ser Gly Ser Ser Thr Leu His Tyr Ala Asp Thr Val Lys Gly
            180                 185                 190

Arg Phe Thr Ile Ser Arg Asp Asn Pro Lys Asn Thr Leu Phe Leu Gln
        195                 200                 205
```

-continued

```
Met Thr Ser Leu Arg Ser Glu Asp Thr Ala Met Tyr Tyr Cys Ala Arg
    210                 215                 220

Trp Gly Asn Tyr Pro His Tyr Ala Met Asp Tyr Trp Gly Gln Gly Thr
225                 230                 235                 240

Ser Val Thr Ala Ser Ser Ala Lys Thr Thr
                245                 250
```